(12) United States Patent
Seidemann et al.

(10) Patent No.: US 8,044,244 B2
(45) Date of Patent: Oct. 25, 2011

(54) PROCESS FOR PREPARING AROMATIC AMINES IN A FLUIDIZED-BED REACTOR

(75) Inventors: Lothar Seidemann, Brussels (BE); Lucia Koenigsmann, Stuttgart (DE); Christian Schneider, Mannheim (DE); Ekkehard Schwab, Neustadt (DE); Dieter Stuetzer, Dudenhofen (DE); Celine Liekens, Edegem (BE)

(73) Assignee: BASF SE, Ludwigshafen (DE)

( * ) Notice: Subject to any disclaimer, the term of this patent is extended or adjusted under 35 U.S.C. 154(b) by 321 days.

(21) Appl. No.: 12/441,907

(22) PCT Filed: Sep. 14, 2007

(86) PCT No.: PCT/EP2007/059703
§ 371 (c)(1),
(2), (4) Date: Mar. 19, 2009

(87) PCT Pub. No.: WO2008/034770
PCT Pub. Date: Mar. 27, 2008

(65) Prior Publication Data
US 2010/0048955 A1     Feb. 25, 2010

(30) Foreign Application Priority Data
Sep. 19, 2006 (EP) ..................... 06120885

(51) Int. Cl.
*C07C 209/00* (2006.01)
(52) U.S. Cl. ..................................... 564/421
(58) Field of Classification Search ......... None
See application file for complete search history.

(56) References Cited

U.S. PATENT DOCUMENTS

| | | | |
|---|---|---|---|
| 3,136,818 A | 6/1964 | Sperber et al. | |
| 3,429,654 A * | 2/1969 | Wilhelm et al. | 549/249 |
| 3,482,946 A | 12/1969 | Shirk | |
| 4,265,834 A | 5/1981 | Birkenstock et al. | |
| 4,430,302 A * | 2/1984 | Krause | 422/144 |
| 5,073,236 A | 12/1991 | Gelbein et al. | |
| 5,112,593 A | 5/1992 | Itoh et al. | |
| 7,098,366 B2 | 8/2006 | Sigl et al. | |
| 7,434,794 B2 * | 10/2008 | Kehrer et al. | 261/112.2 |
| 7,476,297 B2 | 1/2009 | Kaibel et al. | |
| 2003/0106837 A1 * | 6/2003 | Kaibel et al. | 208/46 |
| 2005/0249648 A1 | 11/2005 | Kehrer et al. | |
| 2007/0183963 A1 | 8/2007 | Seidemann et al. | |
| 2007/0202035 A1 | 8/2007 | Walsdorff et al. | |

FOREIGN PATENT DOCUMENTS

| | | |
|---|---|---|
| DE | 1114820 | 10/1961 |
| DE | 1 133 394 | 7/1962 |
| DE | 28 49 002 | 5/1980 |
| DE | 102 26 120 | 12/2003 |
| DE | 10 2004 014 677 | 10/2005 |
| EP | 0 331 465 | 9/1989 |
| EP | 0 428 265 | 5/1991 |
| EP | 1 477 224 | 11/2004 |
| WO | 2005 077520 | 8/2005 |

OTHER PUBLICATIONS

Diao, Shigang et al., "Gaseous catalytic hydrogenation of nitrobenzene to aniline in a two-stage fluidized bed reactor", Applied Catalysis A: General, Elsevier, vol. 286, pp. 30-35, (2005).

\* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

A process for preparing aromatic amines by catalytic hydrogenation of the corresponding nitro compound in a fluidized-bed reactor, in which a gaseous reaction mixture comprising the nitro compound and hydrogen flows from the bottom upward through a heterogeneous particulate catalyst forming a fluidized bed, wherein the fluidized bed is provided with internals which divide the fluidized bed into a plurality of cells arranged horizontally in the fluidized-bed reactor and a plurality of cells arranged vertically in the fluidized-bed reactor, with the cells having cell walls which are permeable to gas and have openings which ensure an exchange number of the heterogeneous, particulate catalyst in the vertical direction in the range from 1 to 100 liters/hour per liter of reactor volume, is proposed.

14 Claims, 2 Drawing Sheets

PROCESS FOR PREPARING AROMATIC AMINES IN A FLUIDIZED-BED REACTOR

Figure 1:
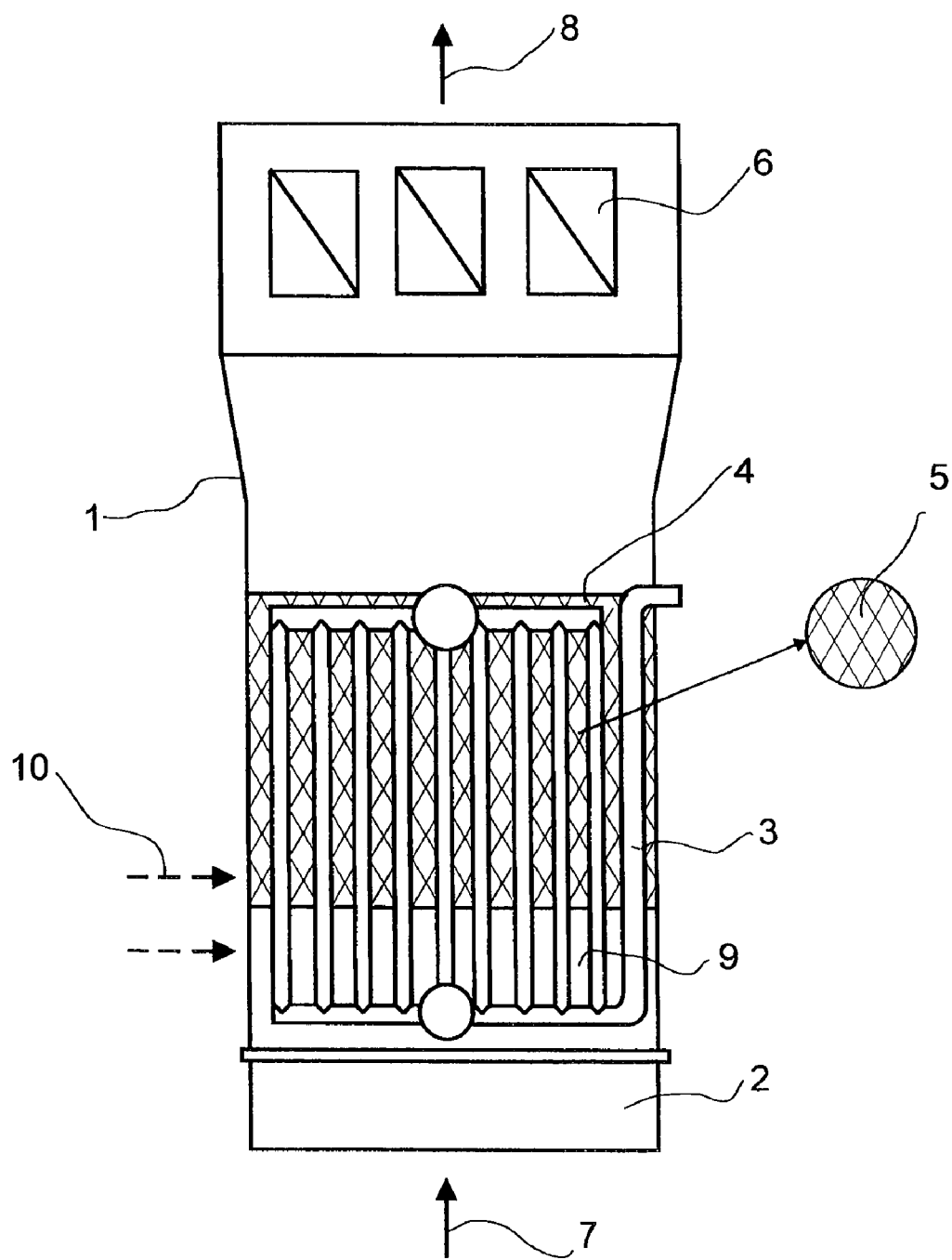

The invention relates to a process for preparing aromatic amines by catalytic hydrogenation of the corresponding nitro compounds in a fluidized-bed reactor, in particular for preparing aniline by catalytic hydrogenation of nitrobenzene.

DE-A 2 849 002 discloses a process for the catalytic gas-phase hydrogenation of aromatic amines over palladium-comprising supported catalysts which is preferably carried out in tube reactors, in which the heat of reaction is removed by means of a suitable heat transfer fluid whose temperature is kept in a range from about 150 to 350° C. A disadvantage is the limited heat removal which is possible: the possible heat fluxes for the removal of heat of reaction by means of a heat transfer medium are in the range from 0.5 to 5 kW per square meter for fixed-bed supported catalysts, so that in the case of strong exothermic reactions, especially the hydrogenation of nitrobenzene to aniline, the removal of the heat of reaction comes up against difficulties when using a tube reactor.

It has accordingly been proposed that the hydrogenation to prepare aromatic amines be carried out in fluidized-bed reactors which are known for their very good heat transfer properties. Such processes are described, for example, in DE-A 1 114 820 and DE A 1 133 394: according to the documents cited, possible hydrogenation catalysts are the heavy metals of groups 1 and 5 to 7 of the Periodic Table and also the iron and platinum group, for example copper, molybdenum, tungsten, nickel, cobalt or mixtures thereof, and their oxides, sulfides or halides, if appropriate together with boron or boron compounds. The catalysts can be applied to various supports. The catalysts have a small particle size, for example 0.3 mm, and are kept in swirling motion by the starting mixture to be hydrogenated and the hydrogen necessary for the hydrogenation, if appropriate, in admixture with an inert gas.

The process of the main patent DE-A 114 820 is carried out under atmospheric pressure, unlike the process of the supplementary patent DE-A 1 133 194 which is carried out at an elevated pressure of at least 3 atmospheres gauge pressure, with a longer life of the catalyst being said to be achieved.

Owing to the very good heat removal properties of a fluidized bed, where heat fluxes in the range from 10 to 100 W per square meter can be achieved for the removal of heat of reaction, the fluidized-bed reactor can be designed considerably more easily for the favored isothermal reaction mode compared to tube reactors which have to be cooled in a complicated fashion.

However, a fluidized bed has disadvantages in terms of mass transfer, since the contact between catalyst and reactants is limited in a known way by the formation of gas bubbles comprising little solid. As a result, part of the aromatic nitro compounds does not come into contact with the swirling supported catalyst and it leaves the reaction zone unreacted. This not only reduces the conversion but also results in further disadvantages: for example, unreacted nitrobenzene in the aniline interferes in the preparation of diphenylmethanediisocyanate (MDI), which is an important intermediate in the polyurethane value-added chain.

It was therefore an object of the invention to achieve a further improvement in the process for preparing aromatic amines by catalytic hydrogenation of the corresponding nitro compounds in a fluidized-bed reactor.

The object is achieved by a process for preparing aromatic amines by catalytic hydrogenation of the corresponding nitro compound in a fluidized-bed reactor, in which a gaseous reaction mixture comprising the nitro compound and hydrogen flows from the bottom upward through a heterogeneous particulate catalyst forming a fluidized bed, wherein the fluidized bed is provided with internals which divide the fluidized bed into a plurality of cells arranged horizontally in the fluidized-bed reactor and a plurality of cells arranged vertically in the fluidized-bed reactor, with the cells having cell walls which are permeable to gas and have openings which ensure an exchange number of the heterogeneous, particulate catalyst in the vertical direction in the range from 1 to 100 liters/hour per liter of reactor volume.

It has been found that it is important to divide the fluidized bed into cells, i.e. hollow spaces enclosed by cell walls, by means of internals both in the horizontal direction and in the vertical direction, with the cell walls being permeable to gas and having openings which allow solids exchange in the vertical direction in the fluidized-bed reactor. Furthermore, the cell walls can be provided with openings which allow solids exchange in the horizontal direction. The heterogeneous particulate catalyst can thus move in the vertical direction and possibly also in the horizontal direction through the fluidized-bed reactor, but is held back in the individual cells compared to a fluidized bed without these, with the above-defined exchange numbers being ensured.

The exchange number is determined by the use of radioactively labeled solid tracer particles which are introduced into the fluidized reaction system, as described, for example, in: G. Reed "Radioisotope techniques for problem-solving in industrial process plants", Chapter 9 ("Measurement of residence times and residence-time distribution"), p. 112-137, (J. S. Charlton, ed.), Leonard Hill, Glasgow and London 1986, (ISBN 0-249-44171-3). Recording of the time and location of these radioactively labeled particles enables the solids motion to be determined locally and the exchange number to be derived (G. Reed in: "Radioisotope techniques for problem-solving in industrial process plants", Chapter 11 ("Miscellaneous radiotracer applications", 11.1. "Mixing and blending studies"), p. 167-176, (J. S. Chariton, ed.), Leonard Hill, Glasgow and London 1986, (ISBN 0-249-44171-3).

Targeted selection of the geometry of the cells enables the residence time of the heterogeneous particulate catalyst in these to be matched to the characteristics of the reaction to be carried out in the particular case.

The series arrangement of a plurality of cells, i.e., in particular from 0 to 100 cells or else from 10 to 50 cells, per meter of bed height, i.e. in the vertical direction in the direction of gas flow from the bottom upward through the reactor, limits backmixing and thus improves the selectivity and the conversion. The additional arrangement of a plurality of cells, i.e. from 10 to 100 cells or else from 10 to 50 cells, per meter in the horizontal direction in the fluidized-bed reactor, i.e. cells through which the reaction mixture flows in parallel or in series, allows the capacity of the reactor to be matched to requirements. The capacity of the reactor of the invention is thus not limited and can be matched to specific requirements, for example for reactions on an industrial scale.

As a result of the cells enclosing hollow spaces which accommodate the particulate heterogeneous catalyst, the cell material itself takes up only a limited part of the cross section of the fluidized-bed reactor, in particular only from about 1 to 10% of the cross-sectional area of the fluidized-bed reactor, and therefore does not lead to the disadvantages associated with increased occupation of the cross section which are known in the case of the internals from the prior art.

The fluidized-bed reactor used in the process of the invention is, as is customary, supplied with the gaseous starting materials from the bottom via a gas distributor. On passing through the reaction zone, the gaseous starting materials are partially reacted over the heterogeneous particulate catalyst which is fluidized by the gas flow. The partially reacted starting materials flow into the next cell where they undergo a further partial reaction.

Above the reaction zone, there is a solids separation device which separates the entrained catalyst from the gas phase. The reacted product leaves the fluidized-bed reactor according to the invention at its upper end in solids-free form.

In addition, the fluidized-bed reactor used according to the invention can be additionally supplied with liquid starting materials either from the bottom or from the side. However, these have to be able to vaporize immediately at the point where they are introduced in order to ensure the fluidizability of the catalyst.

The aromatic amine prepared by the process of the invention is preferably aniline and the corresponding nitro compound is therefore preferably nitrobenzene.

As catalysts, it is possible to use the known, particulate, supported or unsupported catalysts for the hydrogenation of aromatic amines, in particular catalysts comprising heavy metals of the first and/or fifth to eighth group of the Periodic Table, preferably one or more of the elements copper, palladium, molybdenum, tungsten, nickel and cobalt.

The geometry of the cells is not restricted; the cells can be, for example, cells having round walls, in particular hollow spheres, or cells having angular walls. If the walls are angular, the cells preferably have no more than 50 corners, preferably no more than 30 corners and in particular no more than 10 corners.

The cell walls in the cells of the internals are permeable to gas so as to ensure fluidization of the heterogeneous particulate catalyst as a result of flow of the gas phase through the cells. For this purpose, the cell walls can be made of a woven mesh or else of sheet-like materials which have, for example, round holes or holes of another shape.

Here, the mean mesh opening of the woven meshes used or the preferred width of the holes in the cell walls is, in particular, from 50 to 1 mm, more preferably from 10 to 1 mm and particularly preferably from 5 to 1 mm.

As internals in the fluidized bed, particular preference is given to using cross-channel packings, i.e. packings having creased gas-permeable metal sheets, expanded metal sheets or woven meshes which are arranged in parallel to one another in the vertical direction in the fluidized-bed reactor and have creases which form flat areas between the creases having an angle of inclination to the vertical which is different from zero, with the flat areas between the creases of successive metal sheets, expanded metal sheets or woven meshes having the same angle of inclination but with the opposite sign so as to form cells which are delimited in the vertical direction by constrictions between the creases.

Examples of cross-channel packings are the packings of the types Mellpack®, CY or BX from Sulzer AG, CH-8404 Winterthur, or the types A3, BSH, B1 or M from Monz GmbH, D-40723 Hilden.

In the cross-channel packings, hollow spaces, i.e. cells, delimited by constrictions between the creases are formed in the vertical direction between two successive metal sheets, expanded metal sheets or woven meshes as a result of the creased structure of these.

The mean hydraulic diameter of the cells, determined by means of the radioactive tracer technique which is, for example, described above in the reference cited in connection with the determination of the exchange number, is preferably in the range from 500 to 1 mm, more preferably from 100 to 5 mm and particularly preferably from 50 to 5 mm.

Here, the hydraulic diameter is defined in a known manner as four times the horizontal cross-sectional area of the cell divided by the circumference of the cell viewed from above.

The mean height of the cells, measured in the vertical direction in the fluidized-bed reactor by means of the radioactive tracer technique, is preferably from 100 to 1 mm, more preferably from 100 to 3 mm and particularly preferably from 40 to 5 mm.

The above cross-channel packings occupy only a small part of the cross-sectional area of the fluidized-bed reactor, in particular a proportion of from about 1 to 10% of this.

The angles of inclination to the vertical of the flat areas between the creases are preferably in the range from 10 to 80°, in particular from 20 to 70°, particularly preferably from 30 to 60°.

The flat areas between the creases in the metal sheets, expanded metal sheets or woven meshes preferably have a crease height in the range from 100 to 3 mm, particularly preferably from 40 to 5 mm, and a spacing of the constrictions between the creases in the range from 50 to 2 mm, particularly preferably from 20 to 3 mm.

In order to achieve targeted control of the reaction temperature, heat exchangers can be installed in the internals forming the cells for the purpose of introducing heat in the case of endothermic reactions or removing heat in the case of exothermic reactions. The heat exchangers can, for example, be configured in the form of plates or tubes and be arranged vertically, horizontally or in an inclined fashion in the fluidized-bed reactor.

The heat transfer areas can be matched to the specific reaction; in this way, any reaction can be implemented in heat engineering terms by means of the reactor concept according to the invention.

The internals forming the cells are preferably made of materials having a very good thermal conductivity so that heat transport via the cell walls is not hindered. The heat transfer properties of the reactor according to the invention must correspond to those of a conventional fluidized-bed reactor.

The materials for the internals forming the cells should also have a sufficient stability under reaction conditions; in particular, not only the resistance to chemical and thermal stresses but also the resistance of the material to mechanical attack by the fluidized catalyst have to be taken into account.

Owing to the ease of working them, metal, ceramic, polymers or glass materials are particularly useful.

The internals are preferably configured so that they divide from 10 to 90% by volume of the fluidized bed into cells.

Here, the lower region of the fluidized bed in the flow direction of the gaseous reaction mixture is preferably free of internals.

The internals which divide the fluidized bed into cells are particularly preferably located above the heat exchanger. This enables, in particular, the residue conversion to be increased.

As a result of the limited occupation of the cross section by the internals forming the cells, the reactor according to the invention does not have any disadvantages in respect of demixing and discharge tendency of the fluidized particulate catalyst.

The invention is illustrated below with the aid of a drawing.

Figure 2:
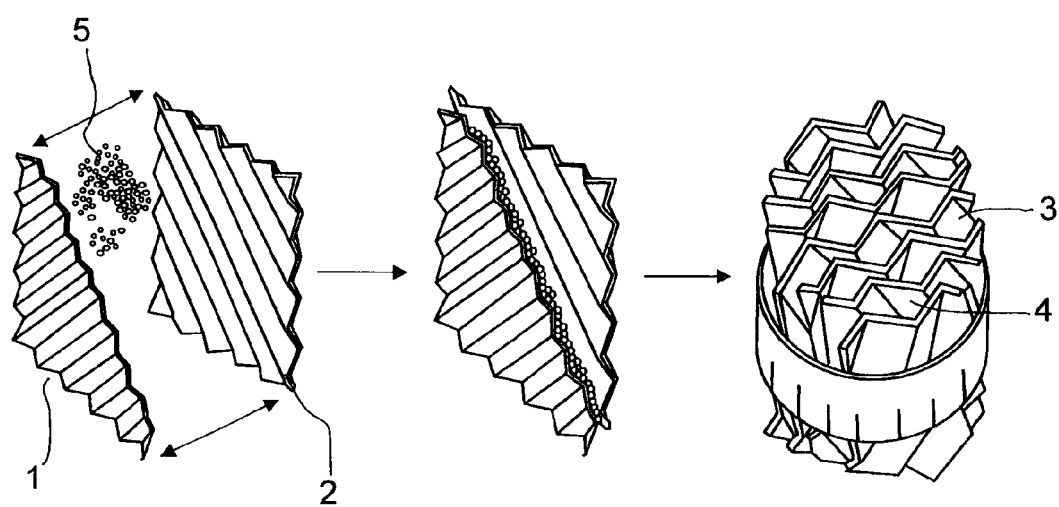

In the drawing:

FIG. 1 schematically shows a preferred embodiment of a fluidized-bed reactor used according to the invention, and FIG. 2 schematically shows a preferred embodiment of internals used according to the invention.

The fluidized-bed reactor 1 shown in FIG. 1 comprises a solids-free gas distributor zone 2, internals 3 which form cells 4 and a heat exchanger 5 in the region of the internals 3.

Above the reaction zone, the reactor widens and has at least one solids separator 6. The arrow 7 indicates the introduction of the gaseous starting materials and the arrow 8 indicates the discharge of the gaseous product stream. Additional liquid-phase starting materials can be introduced at the side, via the broken-line arrows 9.

FIG. 2 shows a preferred embodiment of internals 3 according to the invention in the form of a cross-channel packing having creased metal sheets 10 which are arranged parallel to one another in the longitudinal direction and have creases 11 which divide the metal sheet 10 into flat areas 12 between the creases, with two successive metal sheets being arranged so that they have the same angle of inclination but with the opposite sign and thus form cells 4 which are delimited in the vertical direction by constrictions 13.

The invention claimed is:

1. A process for preparing aromatic amines by catalytic hydrogenation of the corresponding nitro compound in a fluidized-bed reactor, in which a gaseous reaction mixture comprising the nitro compound and hydrogen flows from the bottom upward through a heterogeneous particulate catalyst forming a fluidized bed, wherein the fluidized bed is provided with internals which divide the fluidized bed into a plurality of cells arranged horizontally in the fluidized-bed reactor and a plurality of cells arranged vertically in the fluidized-bed reactor, with the cells having cell walls which are permeable to gas and have openings which ensure an exchange number of the heterogeneous, particulate catalyst in the vertical direction in the range from 1 to 100 liters/hour per liter of reactor volume, wherein the internals are configured as cross-channel packing having creased gas-permeable metal sheets, expanded metal sheets or woven meshes which are arranged in parallel to one another in the vertical direction in the fluidized-bed reactor and have creases which form flat areas between the creases having an angle of inclination to the vertical which is different from zero, with the flat areas between the creases of successive metal sheets, expanded metal sheets or woven meshes having the same angle of inclination but with the opposite sign so as to form cells which are delimited in the vertical direction by constrictions between the creases.

2. The process according to claim 1, wherein the aromatic amine is aniline and the corresponding nitro compound is nitrobenzene.

3. The process according to claim 1, wherein supported or unsupported catalysts comprising heavy metals of one or more of the elements copper, palladium, molybdenum, tungsten, nickel, and cobalt, are used as catalysts.

4. The process according to claim 1, wherein the openings in the cell walls of the cells arranged in the fluidized-bed reactor ensure an exchange number of the heterogeneous particulate catalyst, wherein the openings in the cell walls of the cells arranged in the fluidized-bed reactor ensure an exchange number of the heterogeneous particulate catalyst in the vertical direction in the range from 10 to 50 liters/hour per liter of reactor volume and in the horizontal direction of zero or from 10 to 50 liters/hour per liter of reactor volume.

5. The process according to claim 1, wherein the angle of inclination to the vertical of the flat areas between the creases is in the range from 10 to 80°.

6. The process according to claim 1, wherein the cells of the internals have a hydraulic diameter measured by means of the radioactive tracer technique of from 100 to 5 mm.

7. The process according to claim 1, wherein the cells of the internals have a mean height measured in the vertical direction in the fluidized-bed reactor by means of the radioactive tracer technique of from 100 to 3 mm.

8. The process according to claim 1, wherein the flat areas between the creases in the metal sheets, expanded metal sheets or woven meshes have a crease height in the range from 100 to 3 mm and the spacing of the constrictions between the creases is in the range from 50 to 2 mm.

9. The process according to claim 1, wherein heat exchangers are installed in the internals.

10. The process according to claim 9, wherein the heat exchangers are configured in the form of plates or tubes.

11. The process according to claim 1, wherein the internals are made of metal, ceramic, polymer or glass materials.

12. The process according to claim 1, wherein the internals divide from 10 to 90% by volume of the fluidized bed into cells.

13. The process according to claim 11, wherein the lower region of the fluidized bed in the flow direction of the gaseous reaction mixture is free of internals.

14. The process according to claim 9, wherein the internals which divide the fluidized bed into cells are located above the heat exchangers.

* * * * *